(12) United States Patent
Kataoka

(10) Patent No.: US 11,850,145 B2
(45) Date of Patent: Dec. 26, 2023

(54) INTRAOCULAR LENS FIXING DEVICE

(71) Applicant: Takuya Kataoka, Aichi (JP)

(72) Inventor: Takuya Kataoka, Aichi (JP)

( * ) Notice: Subject to any disclaimer, the term of this patent is extended or adjusted under 35 U.S.C. 154(b) by 470 days.

(21) Appl. No.: 17/079,139

(22) Filed: Oct. 23, 2020

(65) Prior Publication Data

US 2021/0038368 A1    Feb. 11, 2021

Related U.S. Application Data

(63) Continuation of application No. PCT/JP2019/017825, filed on Apr. 25, 2019.

(30) Foreign Application Priority Data

Apr. 26, 2018  (JP) .................................. 2018-085885

(51) Int. Cl.
*A61F 2/16* (2006.01)

(52) U.S. Cl.
CPC ........ *A61F 2/16* (2013.01); *A61F 2002/1681* (2013.01)

(58) Field of Classification Search
None
See application file for complete search history.

(56) References Cited

U.S. PATENT DOCUMENTS

| 6,299,618 B1 | 10/2001 | Sugiura |
| 2007/0027541 A1 | 2/2007 | Aharoni et al. |
| 2012/0130389 A1 | 5/2012 | Prywes |
| 2015/0216652 A1* | 8/2015 | Jansen ................. A61F 2/1648 623/6.43 |
| 2018/0110613 A1* | 4/2018 | Wortz ................... A61F 2/1618 |

FOREIGN PATENT DOCUMENTS

| JP | 2000-229103 A | 8/2000 |
| JP | 2000-245755 A | 9/2000 |
| JP | 2007-029727 A | 2/2007 |
| JP | 2015-223341 A | 12/2015 |
| WO | 2017/134056 A1 | 8/2017 |

OTHER PUBLICATIONS

International Search Report issued in PCT/JP2019/017825 dated Jul. 16, 2019 with English Translation (4 pages).

* cited by examiner

*Primary Examiner* — Leslie Lopez
(74) *Attorney, Agent, or Firm* — j-pat U.S. Patent Legal Services; James Judge

(57) ABSTRACT

An intraocular lens fixing device for fixing in an eyeball an intraocular lens having a plurality of haptics is provided, the intraocular lens fixing device comprising: a linear member stretched in the eyeball; and a plurality of haptic retaining members, each being provided to correspond to and retain each of the plurality of haptics and supported in the space of the eyeball by the linear member, wherein the linear member is secured to each of the plurality of haptic retaining members and the haptic retaining member are made of a flexible material.

10 Claims, 8 Drawing Sheets

INTRAOCULAR LENS FIXING DEVICE

CROSS-REFERENCE TO RELATED APPLICATIONS

This application is a continuation application of International Patent Application No. PCT/JP2019/017825 filed on Apr. 25, 2019, which claims priority to Japanese Patent Application No. 2018-085885 filed on Apr. 26, 2018, the entire contents of which are incorporated by reference.

BACKGROUND OF THE INVENTION

Field of the Invention

The present invention relates to an intraocular lens fixing device or the like used for fixing an intraocular lens.

Description of the Background Art

Crystalline lens reconstruction using an intraocular lens (hereinafter sometimes called "IOL") is widely used as cataract surgery. In reconstructing crystalline lens, the crystalline lens is aspirated by phacoemulsification and aspiration, and then an intraocular lens is fixed in the evacuated lens capsule. However, during the lens reconstruction, the lens capsule is often damaged or lost. In such a case, using surgery such as double-needle fixation or secondary posterior chamber intraocular lens (IOL) implantation, the intraocular lens can be fixed, which, however, requires a high level of surgical technique.

Patent Literature 1 (Japanese Laid-Open Patent Publication No. 2000-245755) describes an intraocular lens fixing device that makes it possible to stably fix the intraocular lens without suturing it. This intraocular lens fixing device comprises a first retaining member to be circumferentially fixed around a ciliary sulcus and a second retaining member for receiving and retaining an intraocular lens, and a joint for integrally joining the first retaining member with the second retaining member.

Further, Patent Literature 2 (Japanese Laid-Open Patent Publication No. 2015-223341) describes a support for supporting an adjustable IOL. The support comprises a frame for housing the adjustable IOL and a leg provided with a bent portion inserted from a ciliary sulcus and hooked onto the outer surface of the sclera. The adjustable IOL is retained with its joint portion of a plurality of lens projecting sidewardly to contact a ciliary body.

SUMMARY OF THE INVENTION

However, with the conventional intraocular lens fixing device, insertion of the intraocular lens into an eyeball is not easy since the member for retaining the intraocular lens is relatively large.

An objective of the present invention is to provide an intraocular lens fixing device for readily inserting into an eyeball members for retaining an intraocular lens.

To solve the above problem, a first aspect of the present invention is to provide an intraocular lens fixing device for fixing in an eyeball an intraocular lens having a plurality of haptics, comprising: a linear member stretched in the eyeball; and a plurality of haptic retaining members, each being provided to correspond to and retain each of the plurality of haptics and supported in the space of the eyeball by being secured to the linear member, wherein the haptic retaining member is a bag-shaped member provided with a port into which the haptic is inserted.

A second aspect of the present invention is to provide an intraocular lens fixing device, wherein the haptic retaining member is made of such a flexible material that the haptic retaining member may contract as much as it passes through a needle hole in a sclera through which the linear member is inserted.

A third aspect of the present invention is to provide an intraocular lens fixing device, wherein the haptic retaining member is provided with a communication hole for communicating the inside of the bag with the outside of the bag.

A fourth aspect of the present invention is to provide an intraocular lens fixing device, wherein the haptic retaining member is made of a meshed material.

A fifth aspect of the present invention is to provide an intraocular lens fixing device, wherein the haptic retaining member is provided with a mark for position adjustment.

A sixth aspect of the present invention is to provide an intraocular lens fixing device, wherein each haptic retaining member is securely provided with the linear member having a needle member attached thereto.

According to the present invention, as a linear member connected to a needle member passes through a sclera, a haptic retaining member fixed to and pulled by the linear member comes close to a needle hole through which the linear member passes. Here the haptic retaining member having flexibility can be formed so as to pass through the needle hole of the sclera, thereby enabling it to pass the haptic retaining member through the needle hole into the eyeball. Then, pulling the linear member is easy. According to the present invention, an intraocular fixing device can be provided which enables it to introduce a haptic retaining member for retaining an intraocular lens into an eyeball.

DESCRIPTION OF THE PREFERRED EMBODIMENTS

The present invention will be described in detail with reference to FIGS. 1 to 13. The following embodiment is one example of the present invention and not intended to limit the scope of the present invention, its applications and its use.

[Configuration of Intraocular Lens Fixing Device]

An intraocular lens fixing device 10 is a tool used for fixing an intraocular lens 20, for example, when a crystalline capsule is damaged or lost in reconstructing a crystalline lens. The intraocular lens fixing device 10 is applicable to an intraocular lens 20 provided with a plurality of haptics 22 at its lens portion 21. The intraocular lens 20 of the present embodiment comprises two haptics 22 projecting outwardly from the circumferential outer surface of the lens portion 21 (see FIG. 2). The two haptics 22 are provided symmetrically with each other with respect to the center of the lens portion 21.

Figure 1:
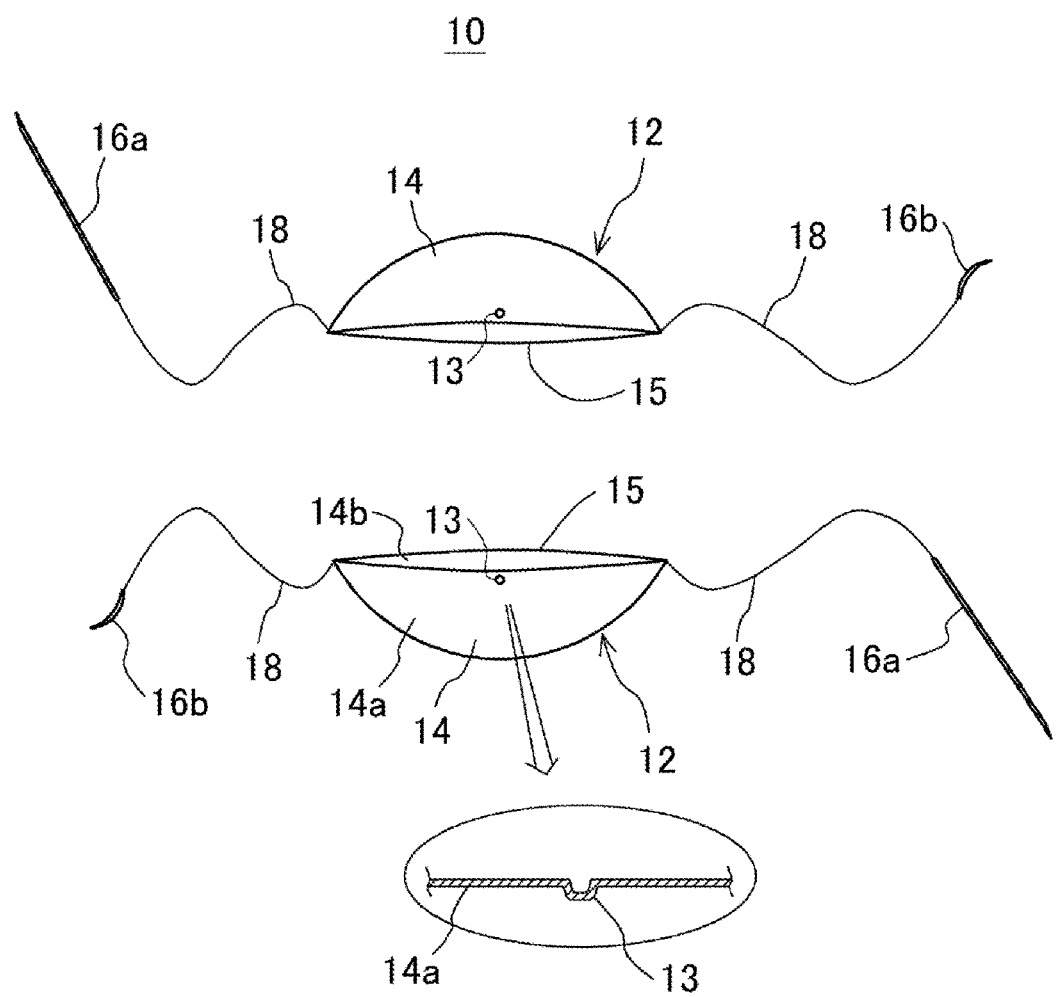
FIG. 1 is a schematic diagram (perspective view) of the intraocular lens fixing device of an embodiment.
Figure 2:
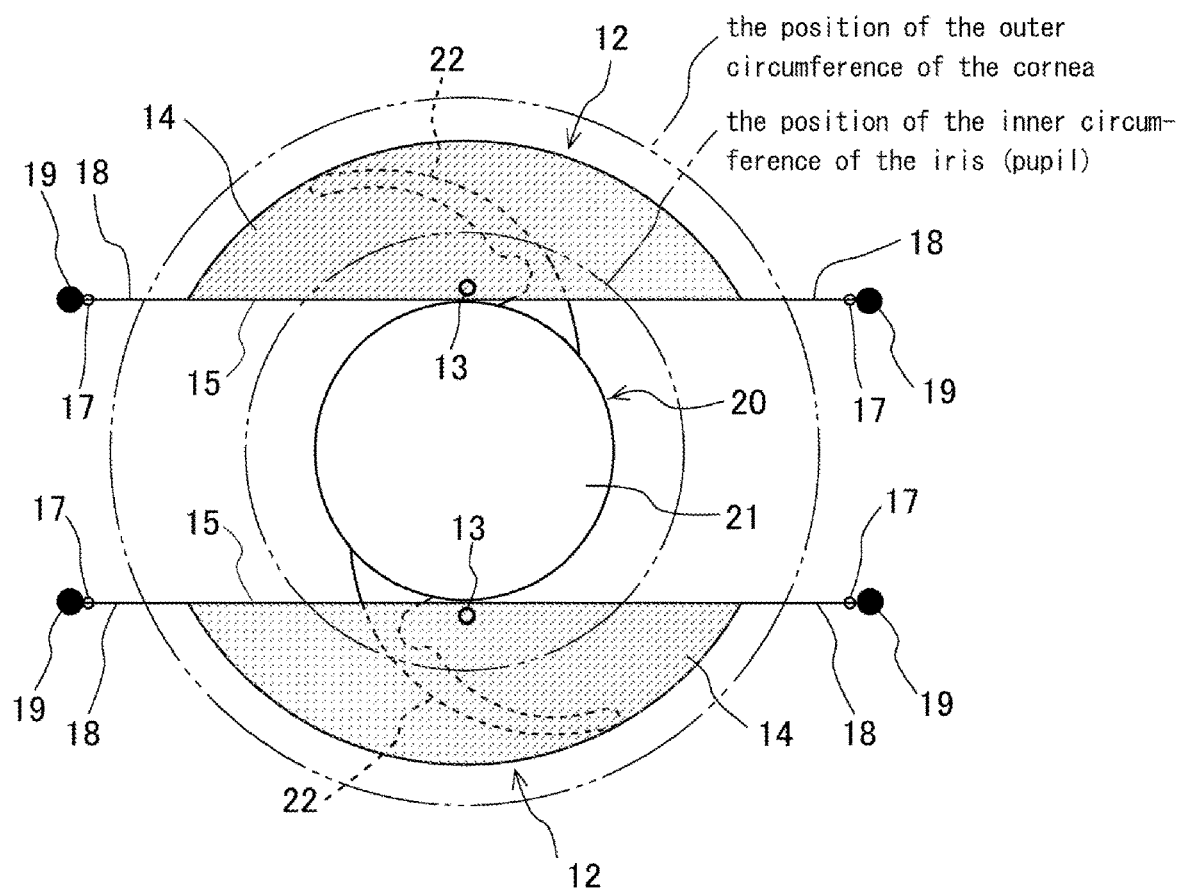
FIG. 2 is a front view showing that an intraocular lens is fixed by the intraocular lens fixing device.

As shown in FIG. 1, the intraocular lens fixing device 10 is comprised by a pair of lens supports 12 each provided with a haptic retaining member 14. Each haptic retaining member 14 corresponds to each of the pair of haptics 22 of the intraocular lens 20 respectively. The pair of haptic retaining members 14 of the intraocular lens fixing device 10 is, as shown in FIG. 2, has ports 15 disposed to face each other in an eyeball 30. And the intraocular lens fixing device 10 fixes the intraocular lens 20 with the pair of the haptic retaining members 14 retaining the pair of haptics 22. To be noted, FIG. 2 is a front view of the eyeball 30 illustrating the inside of the eyeball 30 by a solid line. Further, each haptic retaining member 14 is hatched.

Figure 3:
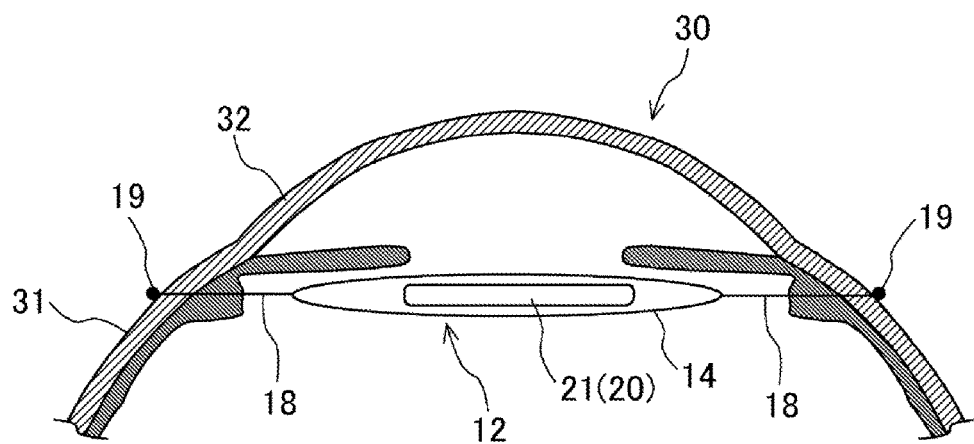
FIG. 3 is a side view showing that the intraocular lens is fixed by the intraocular lens fixing device.

Concerning the front and rear positions (depth), as shown in FIG. 3, the pair of haptic retaining members 14 are disposed slightly rearward of an iris in the eyeball 30 and the intraocular lens 20 is fixed inside a ciliary body. The intraocular lens fixing device 10 will be explained in detail below.

As shown in FIG. 1, in addition to the aforementioned haptic retaining member 14, each lens support 12 comprises two linear members 18, one ends of which are connected to the haptic retaining member 14 and the other ends are connected to needle members 16a and 16b. As the linear member 18, a thread (high-tension thread) is used. The needle member 16a of one linear member 18 is a needle for introducing the linear member 18 and the haptic retaining member 14 into the eyeball 30 with its tip being slightly bent (for example, a needle of about 0.4-0.6 mm in thickness and of about 15 mm in length). The needle member 16b of the other linear member 18 is a needle used exclusively for suturing, and for example a curved surgical (ophthalmological) suturing needle is used (e.g., a suturing needle of about 0.4-0.6 mm in thickness). Further, the two linear members 18 are stretched in the eyeball 30 to floatingly support the haptic retaining member 14 introduced into the eyeball 30.

The pair of the haptic retaining members 14 are the members for retaining the haptics 22 of the intraocular lens 20 as a substitute for the crystalline capsule so as to restrict movement of the intraocular lens 20. Each haptic retaining member 14 is a bag-shaped member (specifically a hammock-shaped member) provided with a port 15 into which the haptic 22 is inserted. It is to be noted that in the following, the direction along which stretch the inner-side sections that form the entrance 15 of each of the haptic retaining members 14 will be referred to as the "longitudinal direction," while the direction along which the longitudinal direction is intersected will be referred to as the "width direction."

The outer-peripheral form of each haptic retaining member 14 is constituted by, in plan view, approximately rectilinear inner-side sections that form the entrance 15, and curvilinear outer-side sections that extend the inter-end interval of the inner-side sections, bulging outward. The outer portion may be a curved portion. To be noted, the inner portion may be, for example, a curved portion having a less curvature than that of the outer portion. Further, each haptic retaining member 14 is comprised by two sheets 14a and 14b of an identical shape, the peripheral portions of which are joined to each other except for the portion forming the port 15.

More specifically, each haptic retaining member 14 is, as shown in FIG. 2, formed to be crescent-shaped in plan view. Each haptic retaining member 14 is formed by joining two crescent-shaped sheets 14a and 14b along their arc-shaped peripheral portions. Joining of the two sheets 14a and 14b is performed by, for example, heat-welding, but another joining method may also be employed. Each haptic retaining member 14 has the other peripheral portion unjointed than the arc-shaped peripheral portion, which form the port 15.

The dimension of each haptic retaining member 14 is that, for example the dimension in the longitudinal direction (length of the port 15) is about 8 mm, the dimension in the width direction is about 2 mm. Further, the diameter of the arc of each haptic retaining member 14 is about 10 mm. To be noted, the dimension of each haptic retaining member 14 is not limited to these figures of this paragraph. The dimension of each haptic retaining member 14 is designed so that the arc formed by the pair of haptic retaining members 14 fixing the intraocular lens 20 be approximately as large as the lens capsule.

For the respective sheets 14a and 14b of each haptic retaining member 14, a thin and ductile material is used (as an example of flexible material). For example, the respective sheets 14a and 14b are made from a resin. For the respective sheets 14a and 14b, for example, a polypyrene membrane of 4 μm in thickness is used. Each haptic retaining member 14 is formed so that it may deformably pass through a needle hole 17 in a sclera 31 through which the needle member 16a passes.

Further, as shown in FIG. 1, each haptic retaining member 14 has its longitudinal opposite ends each connected to one end of each linear member 18. Such joining of the linear member 18 is performed by, for example, heat-welding but another joining method may be employed. For each linear member 18, a thin surgical suture (e.g., a resin suture of 0.02-0.04 mm in thickness) is used. For each linear member 18, for example, polypropylene (e.g. 9-0polypropylene), polyester, PGA or nylon may be used as a material. The other end of each linear member 18 is connected to the foot of the needle members 16a or 16b.

Further, in each haptic retaining member 14 are formed a mark (center mark) for position adjustment in the eyeball 30. The mark 13 is a concavity recessed in the sheet 14a (see the cross section in the ellipsoid of FIG. 1). To prevent the mark 31 from contacting an iris, the mark 31 is formed to be a concavity. Beside the concavity type, the mark 31 may be formed by a through-hole (hole), a notch, a protrusion or an ink-print. For a surgeon who look at the eyeball from outside, the haptic retaining member 14 hides behind the iris and is likely to be invisible partially. The mark 13 is provided so that the position of the haptic retaining member 14 in the eyeball 30 may readily be grasped from outside of the eyeball 30. The mark 31 is disposed in the region inward from the circumference of the haptic retaining member 14. In FIG. 2, the mark 31 is, for example, circular and provided in the center of the haptic retaining member 14 (the center in the longitudinal direction) closely to the port 15. To be noted, the mark 31 may be formed in another location of the haptic retaining member 14 or omitted.

[Use of the Intraocular Lens Fixing Device]

Figure 4:
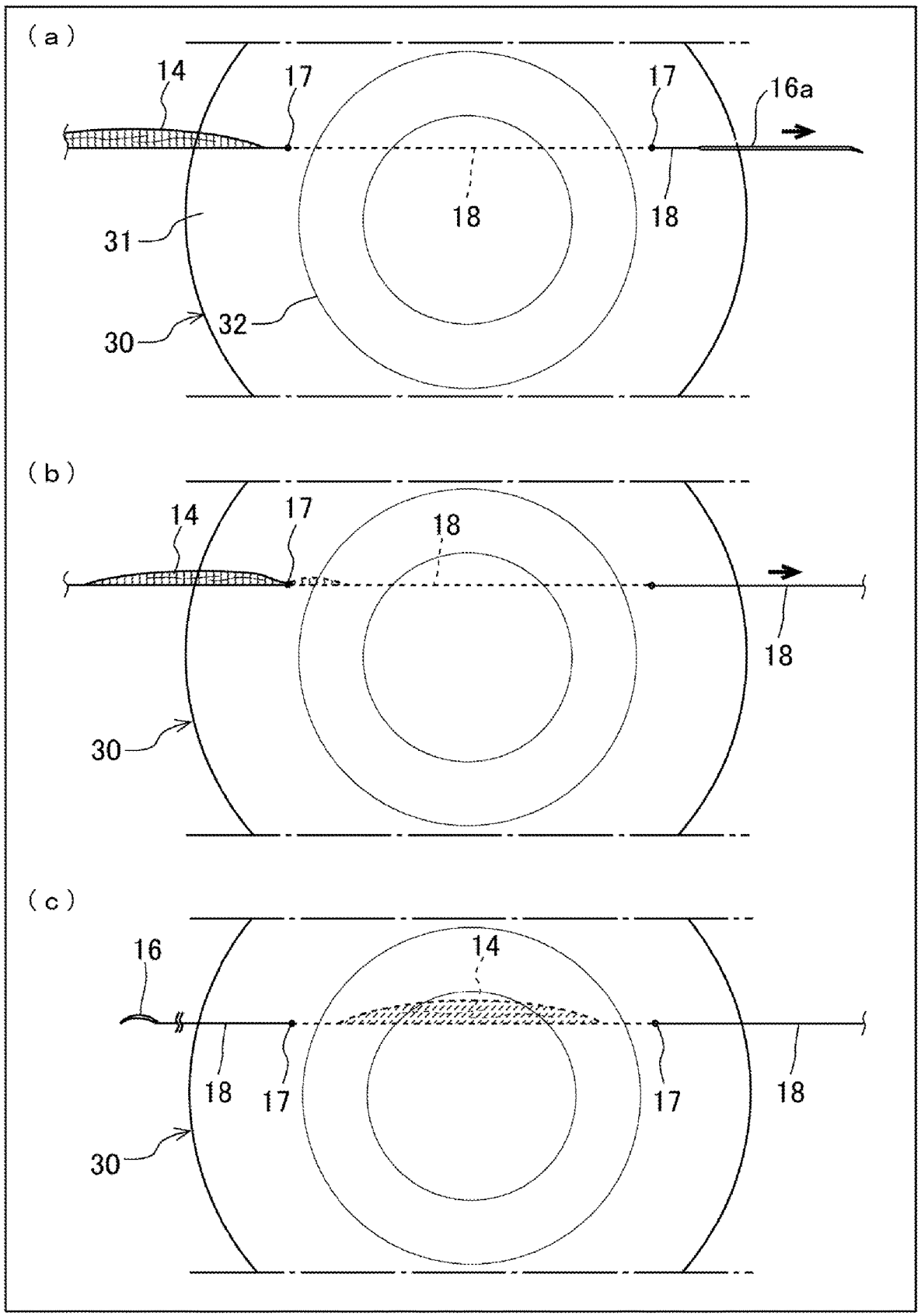
FIG. 4 is a diagram concerning the use of the intraocular lens fixing device and explaining the steps for installing a first lens support.
Figure 5:
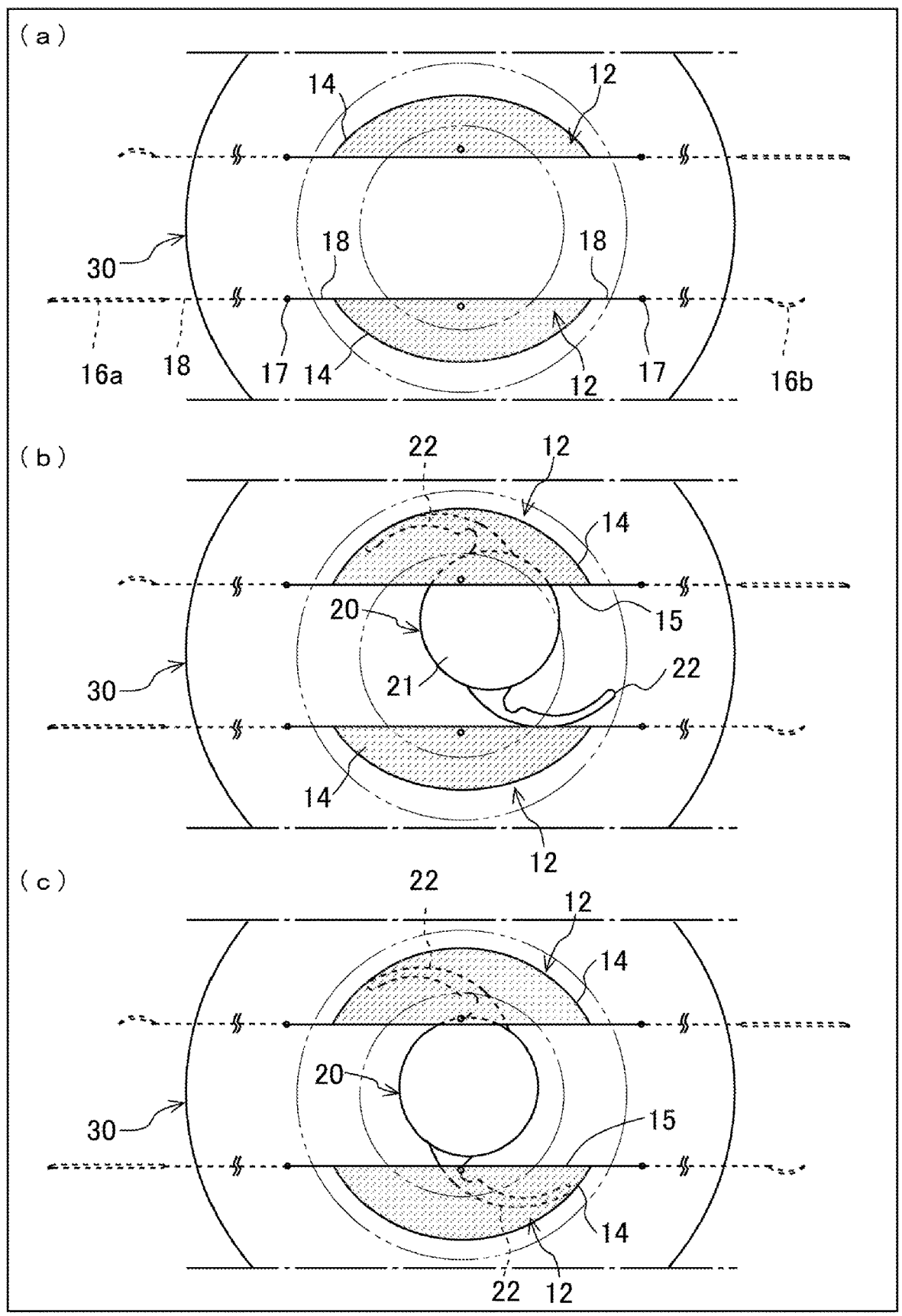
FIG. 5 is a diagram with respect to the use of the intraocular lens fixing device, explaining the steps for inserting a pair of haptics into a pair of haptic retaining members.
Figure 6:
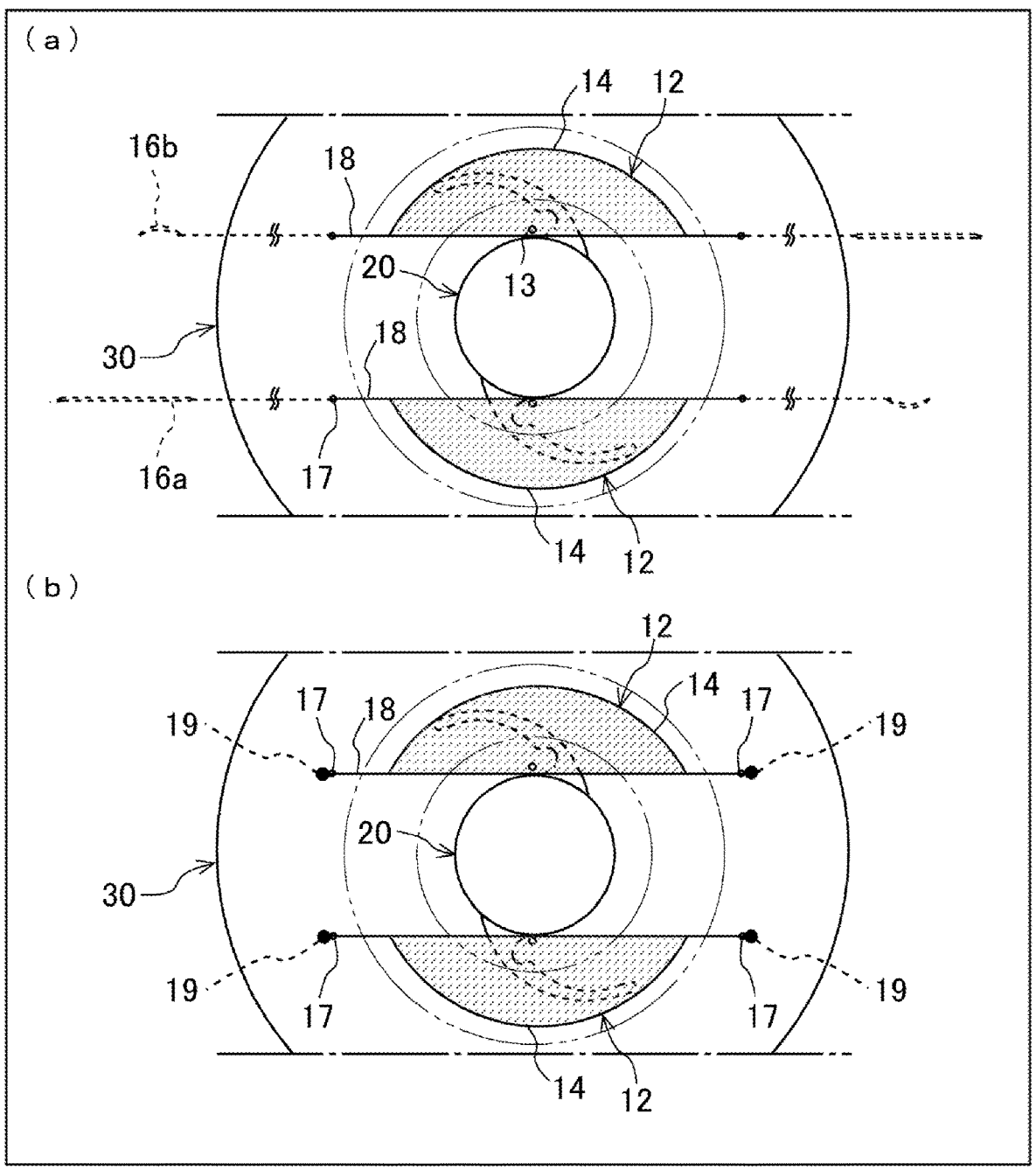
FIG. 6 is a diagram with respect to the use of the intraocular lens fixing device, explaining the steps for fixing the positions of the haptic retaining members.

Referring to FIGS. 4-6, the use of the intraocular lens fixing device 10 will be explained. To be noted, the intraocular lens fixing device 10 of the present embodiment is applicable to both cases where the intraocular lens 20 drops in the eyeball 30 (dislocation of intraocular lens) and where the intraocular lens 20 is inserted into the eyeball 30 from outside. The former case will be described below using an example case where a single-piece multifocal IOL 20 drops.

To be noted, one of a pair of lens supports 12 is called the first lens support 12 and the other called the second lens support 12 below. Further, with respect to the drawings, FIGS. 4-6 are front views of the eyeball. FIG. 4 shows the outside of the eyeball 30 by a solid line and the inside by a broken line, and FIGS. 5-6 show the outside of the eyeball 30 by a broken line and the inside by a solid line. Further, according to the crystalline reconstruction under the present use, excision of a vitreous stalk, followed by excision of tissue attached to the intraocular lens 20, has been done before the intraocular lens fixing device 10 is placed.

Firstly, the surgeon performs the step of introducing into the eyeball 30 the haptic retaining member 14 of the first lens support 12. More specifically, as shown in FIG. 4(a), the surgeon threads the needle member 16a into the eyeball 30 by transscleral suturing. Transscleral suturing is that the surgeon thread the needle member 16a from outside to inside of the eyeball 30. Then, the surgeon inserts the needle member 16a into a pick-up needle (not shown) that was threaded from outside of and to inside of the eyeball 30 through the point located bilaterally symmetrically to the point into which the needle member 16a was threaded. The pick-up needle is hollow. And by removing the pick-up needle together with the needle member 16a toward outside, the needle member 16 can readily be removed from the eyeball 30 to outside. The two points through which the needle member 16a threaded form needle holes 17, respectively.

To be noted, the point through which to thread the needle member 16a is decided so that the haptic retaining member 14 may not overlap the lens portion 21 of the lens support 20 of the fixed intraocular lens 20. For example, where the diameter of the lens portion 21 is 6 mm-7 mm, the needle member 16a is threaded through the left and right points each located 3-4 mm upward from the center of the eyeball 30 and slightly outside from the cornea 32 of the sclera 31 (e.g. each point 1.5 mm-2 mm away from the outer circumference of the cornea 32).

Then, when the surgeon pulls the needle member 16a, as shown in FIG. 4(b), the haptic retaining member 14 contracts (deforms) from its end to become narrow and enters and passes through the needle hole 17 (the left side needle hole 17). The surgeon pulls the needle member 16a to the right side until the haptic retaining member 14 reaches approximately the center in the right and left direction of the eyeball 30. Thereby, the first lens support 12, as shown in FIG. 4(c), is provided in the eyeball 30 such that the haptic retaining member 14 is hung by the two linear members 18 bridged over the two needle holes 17. Then, the surgeon, keeping this state, injects water into the haptic retaining member 14 from the port 15 to expand the haptic retaining member 14. To be noted, instead of water, a gel liquid such as hyaluronic acid may be used.

Then, the surgeon performs the step of introducing into the eyeball 30 the haptic retaining member 14 of the second lens support 12. Under the same step with the first lens support 12, the second lens support 12 is provided vertically symmetrically to the first lens support 12 with respect to the center of the eyeball 30. The second lens support 12 is, as shown in FIG. 5(a), provided in the eyeball 30 such that the haptic retaining member 14 is hung by the two linear members 18 bridged over the two needle holes 17 located 3-4 mm below the center of the eyeball 30. The second lens support 12 is preferably provided generally in parallel to the first lens support 12.

Then, the surgeon picks up the intraocular lens 20 that dropped in the eyeball 30 through an incision hole formed in the sclera 31 of the eyeball 30 using an intraocular forceps (not shown). Then, the surgeon as shown in FIG. 5 (b) inserts one haptic 22 to one haptic retaining member 14 through the port 15. Then, the haptic retaining member 14 is expanded by the haptic 22. Further, as shown in FIG. 5(c), the other haptic 22 is inserted to the other haptic retaining member 14 through the port 15. Likewise, the other haptic retaining member 14 is expanded.

Next, where the center of the intraocular lens 20 is dislocated with respect to the center of the eyeball 30, the surgeon moves the intraocular lens 20 for position adjustment so that the center of the intraocular lens 20 approximately aligns with the center of the eyeball 30. FIG. 6(a) shows that the position of the intraocular lens 20 has been adjusted.

Lastly, the surgeon sutures the linear members 18 to the sclera 31 at the positions immediately outside from the respective needle holes 17 to form knots 19 (see FIG. 6(b)). The linear member 18 extended outside from the knots 19 are cut off. Thereby, the position of each haptic retaining member 14 is secured and the position of the intraocular lens 20 is retained by each haptic member 14. Further, the surgeon sutures the incision used for inserting the forceps. Hence, the reconstruction of crystalline lens is completed.

Effect and the Like

According to the present embodiment, the haptic retaining member 14 for retaining the haptic 22 of the intraocular lens 20 is a bag-shaped member made of ductile material and can pass through the needle hole 17 through which the linear member 18 secured to the haptic retaining member 14 passes and can be introduced into the eyeball 30 through the needle hole 17. Thus, no incision would be made and the haptic retaining member 14 can readily be introduced into the eyeball 30 by just pulling the linear member 18.

Further, according to the present embodiment, by just pulling the linear member 18, the position of each haptic retaining member 14 can be adjusted. Especially, since the mark formed in each haptic retaining member 14 is positioned visibly to the surgeon, the surgeon can install each haptic retaining member 14 at the approximately same position with the lens capsule while looking at the position of the mark 13 Thereby, the intraocular lens 20 can be retained in place.

Further, according to the present embodiment, each haptic 22 of the intraocular lens 20 is softly retained by the bag-shaped haptic retaining member 14. Each haptic 22 does not contact intraocular tissues. Here, the haptic 22 of the single-piece multifocal IOL 20 is thick, thereby often causing inflammation. Further, the haptic 22 is made of a soft material (e.g. flexible acrylic gel), and therefore there is possibility that the haptic 22 is ruptured when directly tied to a suture. In other words, the single-piece multifocal IOL 20 is not suitable to either double-needle fixation or secondary posterior chamber intraocular lens (IOL) implantation. These techniques are applicable to limited types of intraocular lens 20 to be fixed. On the other hand, the present embodiment does not employ these techniques with respect to the single-piece multifocal IOL 20, but a new surgical technique (parallel bar (thread) suturing technique) in which each haptic 22 does not contact intraocular tissues. Thus, inflammation of intraocular tissues can be prevented. Further, according to the present embodiment, the present invention is applicable to various types of intraocular lens 20, including single-piece multifocal IOL 20.

Further, according to the present embodiment, it is possible to decide the installation position (depth) of the pair of haptic retaining members 14 in the fore and rear direction correspondingly to the position at the sclera 31 through which the needle member 16a is threaded. Here, according to the devices described in Patent Literature 1 and Patent Literature 2, the position of the intraocular lens support is limited and therefore the depth of the intraocular lens is limited. On the other hand, according to the present embodiment, the intraocular lens 20 can be fixed at any depth.

Further, according to the present embodiment, the intraocular lens 20 can be inserted into the eyeball 30 from outside, and also the intraocular lens 20 that dropped in the eyeball 30 can be fixed without being removed. In other words, reposition of the intraocular lens 20 can be completed by only intraocular operations.

Modification 1

Figure 7:
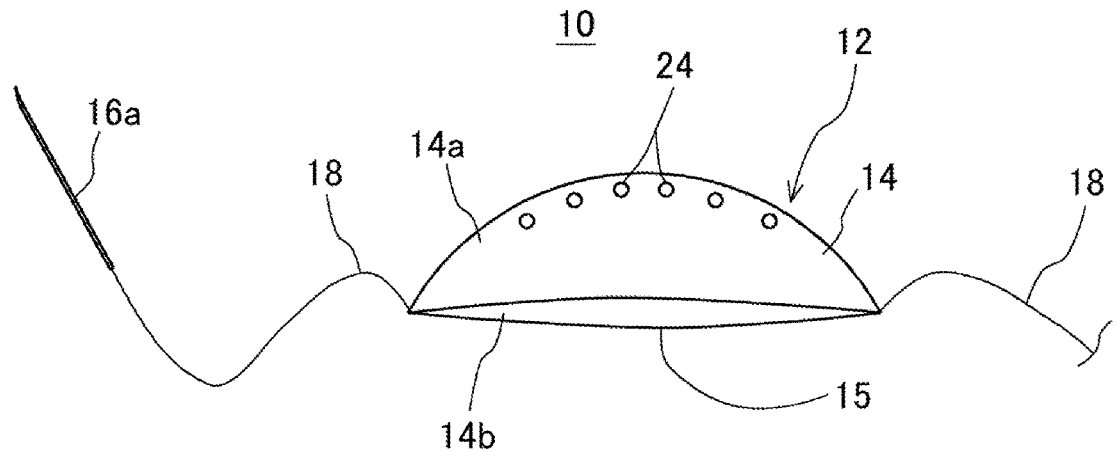
FIG. 7 is a schematic diagram (perspective view) of the intraocular lens fixing device of a modification 1.

According to the present modification, as shown in FIG. 7, communication holes 24 for communicating the outside through the inside of the bag are formed in the respective sheets 14a and 14b of each haptic retaining member 14. The communication holes 24 are formed in plurality. Each communication hole 24 is formed smaller than the cross section of the tip portion of the haptic 22 and therefore the haptic 2 cannot pass therethrough. According to the present modification, each haptic retaining member 14 is of no blind end structure because of the communication holes 24. Thereby, bacteria does not grow readily in each haptic retaining member 14. Further, medication such as antibiotic can efficiently be supplied into each haptic retaining member 14. To be noted, the communication hole 24 may be at least positioned to the arc-shaped periphery or may be formed to the port 15.

Modification 2

Figure 8:
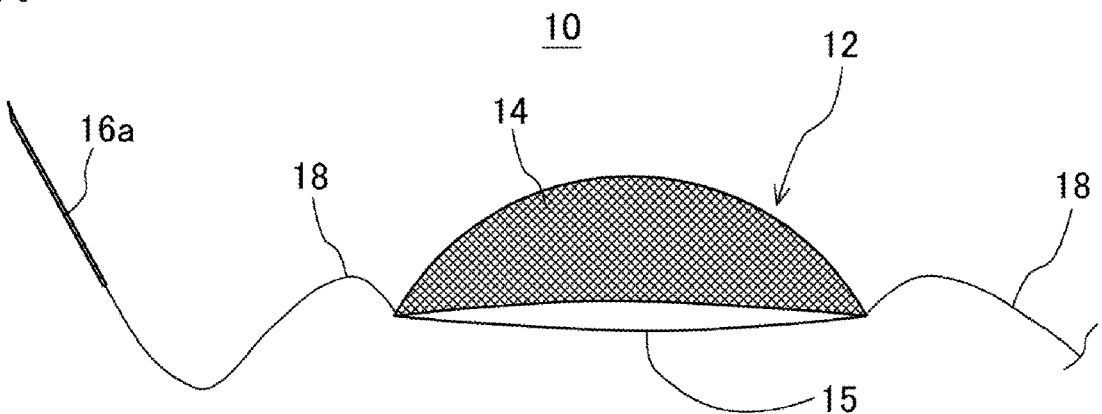
FIG. 8 is a schematic diagram (perspective view) of the intraocular lens fixing device of a modification 2.

According to the present modification, as shown in FIG. 8, each haptic retaining member 14 is made of a meshed and bag-shaped material. The mesh of the haptic retaining member 14 is smaller than the cross section of the tip portion of the haptic 22 and therefore the haptic cannot pass therethrough. According to the present modification, bacteria does not grow readily in each haptic retaining member 14. Further, medication such as antibiotic can efficiently be supplied into each haptic retaining member 14.

Modification 3

Figure 9:
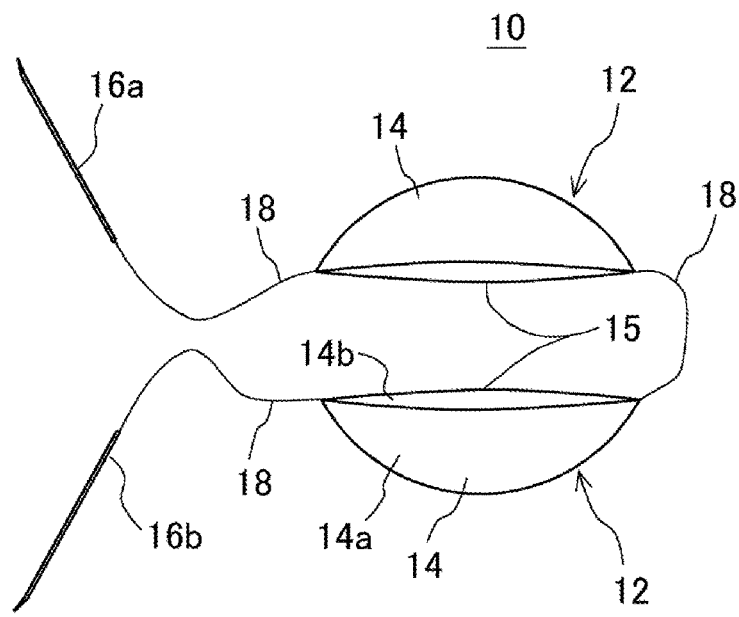
FIG. 9 is a schematic diagram (perspective view) of the intraocular lens fixing device of a modification 3.

According to the present modification, as shown in FIG. 9, the pair of haptic retaining members 14 are integrally connected to each other by the linear member 18. More specifically, the haptic retaining members 14 are provided to be a single thread between the two needle members 16a and 16b. In this case, with the respective needle members 16a and 16b being front ends, each haptic retaining member 14 can be introduced into the eyeball 30. Thereby, sclera suturing on one side is unnecessary.

Modification 4

Figure 10:
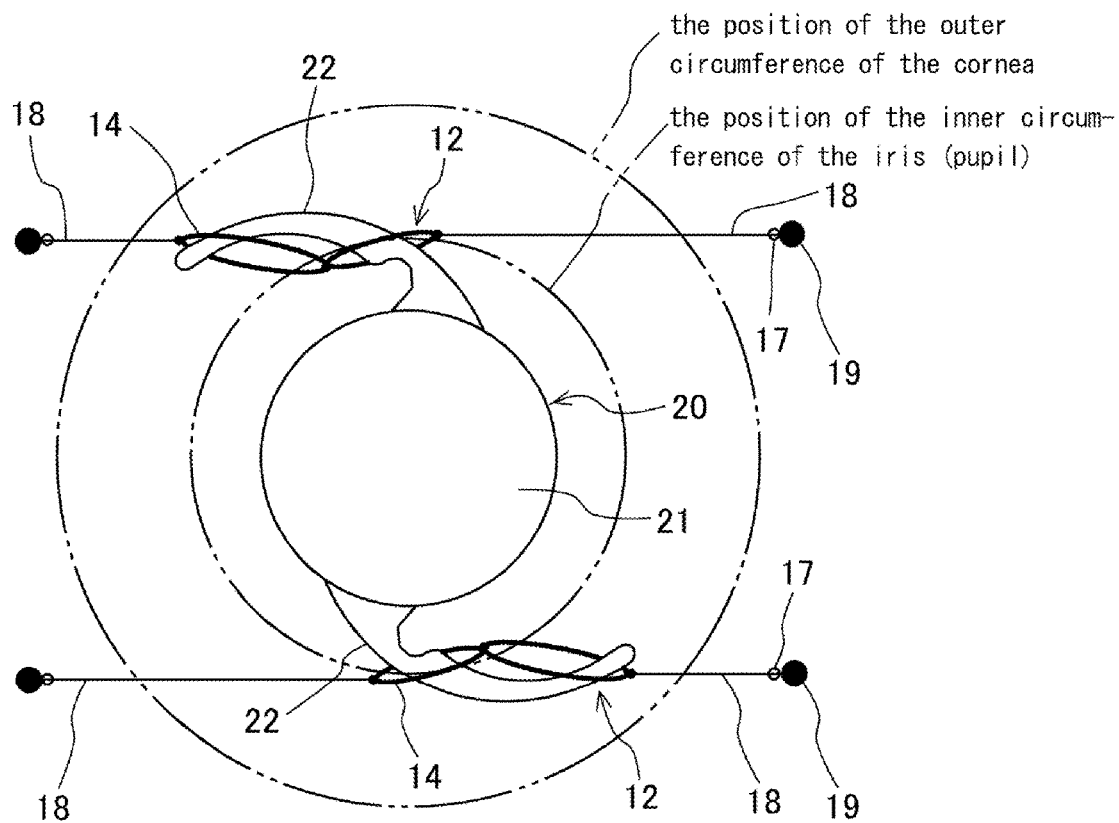
FIG. 10 is a front view showing that the intraocular lens is fixed by the intraocular lens fixing device of a modification 4.

According to the present modification, each haptic retaining member 14 is formed by a member of a shape other than bag-shape. As shown in FIG. 10, each haptic retaining member 14 is constituted by a plurality of ring-shaped portions for hooking the haptic 22. More specifically, each haptic retaining member 14 is a 8-shaped portion (flexible portion) formed by tying a suture. The haptic 22 is retained by the two rings. To be noted, FIG. 10 shows a front view of the eyeball 30 with the inside of the eyeball being indicated by a solid line.

Modification 5

Figure 11:
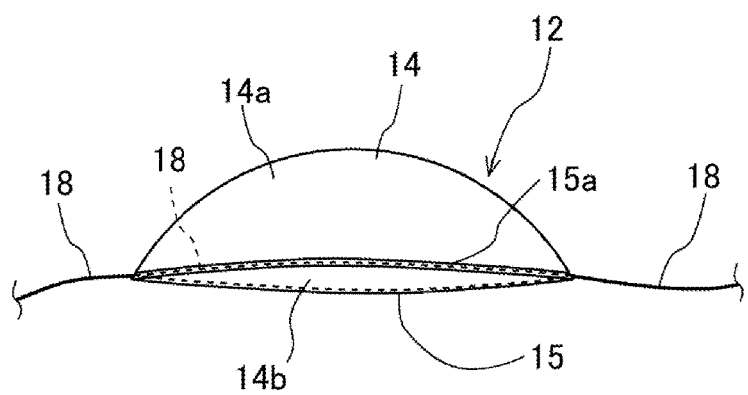
FIG. 11 is a schematic diagram (perspective view) of the intraocular lens fixing device of a modification 5.

According to the present modification, the linear member 18 is provided along the periphery of the port 15 of each haptic retaining member 14. For example, each haptic retaining member 14, as shown in FIG. 11, is provided with pores 15a at the edge of the port 15 of the respective sheets 14a and 14b. The fine pore 15a, for example, is formed by folding the sheets 14a and 14b. The linear member 18 is divided into two lines at one end of the haptic retaining member 14. Each of the two lines passes through the fine pores 15a of the opposite sheet 14a or 14b, and the two lines are combined together at the other end of the haptic retaining member 14. The linear member 18 is secured to the haptic retaining member 14.

To be noted, the linear member 18 does not always need to be provided along the port 15 of both sheets 14a and 14b, but may be provided and secured along the port 15 of one sheet 14a. In this case, the linear member 18 is not divided between the opposite ends of the haptic retaining member 14. Further, the linear member 18 can be secured along the port 15 of the sheet 14a without the fine pore 15a being formed in the sheet 14a.

Modification 6

Figure 12:
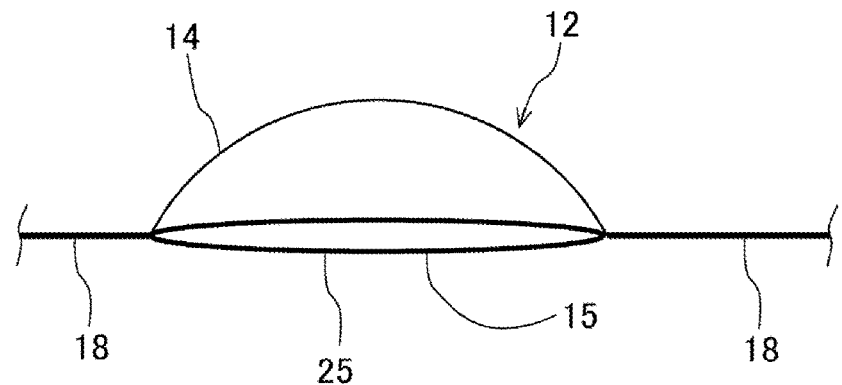
FIG. 12 is a schematic diagram (perspective view) of the main portion of the lens support of the intraocular lens fixing device of a modification 6.
Figure 13:
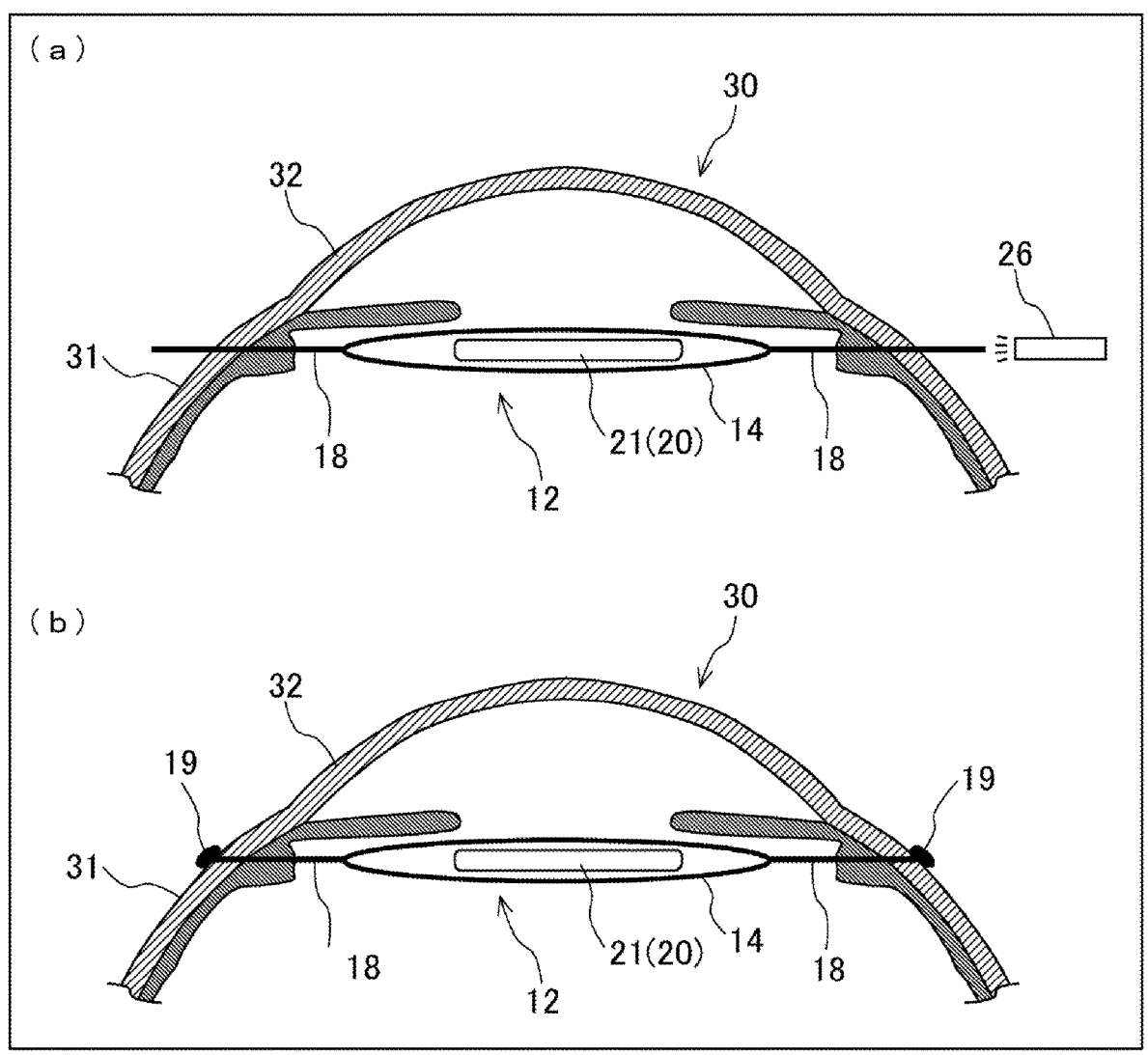
FIG. 13 is a side view of the lens support of a modification. 6.

According to the present modification, the linear member 18 is formed by a thin bar-shaped resin or metal member. As shown in FIG. 12, a edge member 25 (e.g., a member of resin) for securing the linear member 18 may be provided to the haptic retaining member 14. The edge member 25 is provided around all the periphery of the port 15. To be noted, without the edge member 25, the linear member 18 (bar-shaped member) may be secured to the haptic retaining member 14. Further, in the case of using a thread-shaped material as the linear member 18 in the aforementioned embodiment, the edge member 25 may be provided to the haptic retaining member 14.

Here, in the case of using a bar-shaped material as the linear member 18, after the lens support 12 is bridged inside the eyeball 30 and then the positions of the haptic retaining members 14 are adjusted, the ends of the linear members 18 are subjected to heat treatment, namely they are heated using a heating device 26 shown in FIG. 13(a) to form hooks 19 shown in FIG. 13(b). Thereby, the position of the haptic retaining member 14 is readily fixed. The end treatment by heat is not limited to the case of the linear member 18 being bar-shaped, but is applicable to the case of the linear member 18 being thread-shaped.

Modification 7

According to the aforementioned embodiment, the linear members 18 of the intraocular lens fixing device 10 is provided with the needle members 16a and 16b. However, it is possible that when the intraocular lens fixing device 10 is on sale as a product, the needle members 16a and 16b are not attached thereto, but the needle member 16a and 16b are attached by the surgeon when in use.

The invention claimed is:

1. An intraocular lens fixing device for fixing in an eyeball an intraocular lens having a plurality of haptics, the intraocular lens fixing device comprising:
a plurality of independent haptic retaining pouches, each being provided to correspond to and retain each of the plurality of haptics and having an inner side constituting an entrance into which a corresponding one of the plurality of haptics inserts; and
a first filamentary element secured to one of longitudinally opposite end portions of each haptic retaining pouch and a second filamentary element secured to the other of the longitudinally opposite end portions of each haptic retaining pouch, wherein the opposite end portions are along the entrance-constituting inner side of the respective haptic retaining pouches, the first and second filamentary elements for being stretched through the eyeball to support each haptic retaining pouch in a cavity within the eyeball.

2. The intraocular lens fixing device according to claim 1, wherein each haptic retaining pouch is made of a membrane that is flexible such that the haptic retaining pouch contracts to a degree that allows the haptic retaining pouch to pass through a needle hole in a sclera through which the filamentary element is inserted.

3. The intraocular lens fixing device according to claim 2, wherein each haptic retaining pouch is provided with a communication hole penetrating the membrane constituting the haptic retaining pouch, whereby interior and exterior sides of the pouch communicate.

4. The intraocular lens fixing device according to claim 2, wherein the membrane that each haptic retaining pouch is made of is a meshed material.

5. The intraocular lens fixing device according to claim 1, wherein each haptic retaining pouch is provided with a communication hole penetrating a membrane constituting the haptic retaining pouch, whereby interior and exterior sides of the pouch communicate.

6. The intraocular lens fixing device according to claim 1, wherein each haptic retaining pouch is made of a meshed membrane.

7. The intraocular lens fixing device according to claim 1, wherein each haptic retaining pouch is provided with a mark for position adjustment.

8. The intraocular lens fixing device according to claim 1, further comprising a first needle member attached to the first filamentary element and a second needle member attached to the second filamentary element.

9. The intraocular lens fixing device according to claim 1, wherein each haptic retaining pouch has a first flexible membrane and a second flexible membrane whose outer peripheries are closed together except along the entrance-constituting inner side of the pouch.

10. The intraocular lens fixing device according to claim 1, wherein the longitudinally opposite end portions are along the largest diameter of the respective haptic retaining pouches.

\* \* \* \* \*